United States Patent [19]
Brown et al.

[11] Patent Number: 5,855,894
[45] Date of Patent: Jan. 5, 1999

[54] PASTEURELLA HAEMOLYTICA TYPE A-1 BACTERIN-TOXOID VACCINE

[75] Inventors: Albert L. Brown; Krishnaswamy Iyengar Dayalu; Thomas James Kaufman; Rex Steven Newsham, all of Lincoln, Nebr.

[73] Assignee: Pfizer Inc., New York, N.Y.

[21] Appl. No.: 550,051

[22] Filed: Oct. 30, 1995

Related U.S. Application Data

[63] Continuation of Ser. No. 307,613, Sep. 20, 1994, abandoned, which is a continuation of PCT/US93/02930, Mar. 30, 1993, which is a continuation-in-part of Ser. No. 878,146, May 4, 1992, abandoned, which is a continuation-in-part of Ser. No. 869,934, Apr. 16, 1992, abandoned, which is a continuation-in-part of Ser. No. 860,377, Mar. 30, 1992, abandoned.

[51] Int. Cl.$^6$ .................. A61K 39/02; A61K 39/085; A61K 39/102; C12N 7/00
[52] U.S. Cl. ................ 424/236.1; 424/243.1; 424/252.1; 424/184.1; 424/255.1; 424/278.1; 424/823; 435/235.1; 530/350
[58] Field of Search ............... 424/236.1, 243.1, 424/252.1, 184.1, 255.1, 823, 278.1; 435/235.1; 530/350

[56] References Cited

U.S. PATENT DOCUMENTS

| | | |
|---|---|---|
| 4,559,306 | 12/1985 | Kucera . |
| 4,626,430 | 12/1986 | Kucera . |
| 4,681,762 | 7/1987 | Oeschger et al. . |
| 4,957,739 | 9/1990 | Berget et al. . |
| 5,084,269 | 1/1992 | Kullenberg . |
| 5,165,924 | 11/1992 | Shewen et al. . |
| 5,587,166 | 12/1996 | Donachie . |
| 5,665,363 | 9/1997 | Hansen et al. . |

FOREIGN PATENT DOCUMENTS

| | | |
|---|---|---|
| WO 8000412 | 3/1980 | WIPO . |
| WO 9115237 | 10/1991 | WIPO . |
| 9319779 | 10/1993 | WIPO . |

OTHER PUBLICATIONS

Loan, R. W., and Purdy, C. W. 1986, Proc. 14th World Congress on Cattle Diseases, 1:653–658.
Schnepper et al., 1996, Vet. Medicine, 91(1):72–76.
Newsham et al., 1994, Eds. Donachie et al., Third Int'l Conf. on Haemophilus, Actinobacillus, & Pasteurella (HAP94) p. 215, Plenum Press:NY,NY.
Confer et al., 1994, Agri–Practice; 15 (8):10–15.
Confer, 1993, Vet. Microbiology, 37:353–368.
Loan et al., 1989. The Bovine Practitioner, #24 pp. 22–24.
Wilkie et al., 1980. Am. J. Vet. Res. 41(11):1773–1778.
Friend et al., 1977, Can. J. Comp. Med. 41:77–83.
Cardella et al., 1987 Can. J. Vet. Res. 51:204–211.
Yancey et al., 1993. J. Diary Sci, 76:2418–36.
Matsuoka et al., 1972, JAVMA, 163(No. 3):334–337.
Purdy et al., 1996, Am. J. Vet. Res. 57:1168–74.
Jericho et al., 1990, Vaccine 8(4):315–320.
Mosier et al., 1989, Res. Vet. Sci, 47(1):1–10.
Wells et al., Res. Vet Sci. 1979, 27:248–250.
Lo 1990. Can J. Vet. Res. 54 Suppl:S33–S35.
Shewen et al., 1985, Am. J. Vet. Res. 46(5):1212–1214.
Panciera et al., 1984, Am. J. Vet. Res. 45(12):2538–42.
Shewen et al., 1988, Vet. Med. Oct. 1988:1078–83.
Smith The Bovine Practitioneer 1988 #23:31–34.

*Primary Examiner*—Nita Minnifield
*Attorney, Agent, or Firm*—Peter C. Richardson; Paul H. Ginsburg; Alan L. Koller

[57] ABSTRACT

This invention relates to the field of *Pasteurella haemolytica* vaccines. More particularly, the invention relates to a bacterin-toxoid vaccine capable of inducing immunity in bovine species in one dose against *Pasteurella haemolytica* Type A-1 infection comprising *Pasteurella haemolytica* derived leukotoxoid, capsular antigen, soluble antigens and cells, methods to make the vaccine and methods of vaccinating bovine animals.

29 Claims, No Drawings

PASTEURELLA HAEMOLYTICA TYPE A-1 BACTERIN-TOXOID VACCINE

This application is a continuation of application U.S. Ser. No. 08/307,613 filed on Sep. 20, 1994, now abandoned which is a continuation of PCT/US93/02930 filed Mar. 30, 1993 which is a continuation-in-part of U.S. Ser. No. 07/878, 146 filed May 4, 1992 now abandoned which is a continuation-in-part of U.S. Ser. No. 07/869,934 filed Apr. 16, 1992 now abandoned which is a continuation-in-part of U.S. Ser. No. 07/860,377 filed Mar. 30, 1992 now abandoned.

FIELD OF THE INVENTION

This invention relates to the field of *Pasteurella haemolytica* vaccines. More particularly, the invention relates to a bacterin-toxoid vaccine capable of inducing immunity in bovine species in one dose against *Pasteurella haemolytica* Type A-1 infections comprising *Pasteurella haemolytica* derived leukotoxoid, capsular antigen, soluble antigens and inactivated cells, methods to make the vaccine and methods of vaccinating bovine animals.

BACKGROUND OF THE INVENTION

Approximately 40% to 80% of all diseases of cattle involve the respiratory system (Lillie L E: "The bovine respiratory disease complex." *Can Vet J* 15:233–242, 1974). Bovine respiratory disease complex (BRDC) is a major problem in the U.S. cattle industry. BRDC consists of several clinical syndromes, the two most common being shipping fever of feedlot cattle and enzootic calf pneumonia usually seen in dairy calves. While it is now recognized that numerous viruses, stressful management practices, and environmental factors are important in the genesis of shipping fever, *P. haemolytica* biotype A, serotype 1 (Type A-1) is the main bacterial agent responsible for the clinical disease and pathophysiologic events leading to acute fibrinous lobar pleuropneumonia and subsequent death (Yates W D G: "A review of infectious bovine rhinotracheitis, shipping fever pneumonia and viral-bacterial synergism in respiratory disease of cattle." *Can J Comp Med* 46:225–263, 1982).

In a two year study conducted in Saskatchewan, Canada, *P. haemolytica* Type A-1 isolated from the lungs of 74% of cattle that died of shipping fever pneumonia (Schiefer B, Ward G E, Moffatt R E: "Correlation of microbiological and histological findings in bovine fibrinous pneumonia." *Vet Pathol* 15:313–321, 1978). Annual progress reports during the five year period 1987 to 1991 from the Department of Veterinary Science at South Dakota State University (South Dakota State University, Department of Veterinary Science, Animal Disease Research and Diagnostic Laboratory: Annual Progress Reports 1987–1991. Submitted to the NC107 Technical Committee on Bovine Respiratory Disease.) revealed that *P. haemolytica* Type A-1 was isolated from 48.7% of bovine pneumonic lungs. Thus, it appears to be the major bacterial agent causing pneumonia in cattle.

*P. haemolytica* serotype Type A-1 is the pathogen responsible for the fibrinous necrotizing lobar pleuropneumonia seen in shipping fever and purulent bronchopneumonia associated with enzootic calf pneumonia. Interestingly, other *P. haemolytica* serotypes (frequently ST2 and ST4 and occasionally ST7 and ST11) are innocuous inhabitants in many areas of the nasal cavity or upper respiratory tract (URT) of clinically normal feedlot cattle (Frank G H: "When *Pasteurella haemolytica* colonizes the nasal passages of cattle." *Vet Med* 83:1060–1064, 1988 and Wilkie B N, Shewen P E: "Defining the role that *Pasteurella haemolytica* plays in shipping fever." *Vet Med* 83:1053–1058, 1988). In clinically normal dairy calves, *P. multocida* may predominate in the URT flora, in which various serotypes of *P. haemolytica* can also be found. In contrast, *P. haemolytica* Type A-1 is barely detectable in the URT of feedlot and dairy calves (Frank G H: supra (1988) and Wilkie B N, Shewen P E: supra (1988)).

Exposure of calves to stress factors such as viral infection, marketing, shipping, processing at feedlots, and abrupt changes in climate leads to an explosive growth and colonization by *P. haemolytica* Type A-1 in all areas of the URT (Frank G H: supra (1988) and Wilkie B N, Shewen P E: supra (1988)). No other serotype of *P. haemolytica* is known to exhibit this type of increase. In shipping fever pneumonia, colonization of the URT with *P. haemolytica* Type A-1 is an important prerequisite to the development of the clinical disease and the ensuing fibrinous necrotizing lobar pleuropneumonia. Id.

In spite of its potential importance in the pathogenesis of the pneumonia, the mechanism of colonization that facilitates the explosive proliferation of *P. haemolytica* Type A-1 in the URT is poorly understood. It is nevertheless apparent that these organisms enter the lung via aspiration of droplet nuclei, colonized desquamated epithelial cells, or pharyngeal secretions. At the University of Minnesota (Whiteley L O, et al: "*Pasteurella haemolytica* and bovine respiratory disease: Current thoughts on its pathogenesis." *Vet Int Med* 6:1–12, 1992), large numbers of rapidly growing bacteria entering the alveolar spaces were found to interact with alveolar macrophages. The endotoxin released from the bacteria crosses the alveolar wall and activates the pulmonary intravascular macrophages, endothelium, neutrophils, platelets, complement, and Hageman factor leading to complex interactions of cells and inflammatory mediators. Progression of this inflammatory response with neutrophil influx is responsible for the acute lung injury that is associated with the disease. Leukotoxin, one of the major virulence factors of *P. haemolytica,* may enable the bacteria to survive by destroying phagocytic cells and impairing lung clearance mechanisms. Id.

Prevention of pneumonic pasteurellosis has been attempted in the past by the use of killed bacterins of *P. haemolytica.* However, it has been demonstrated that vaccination with bacterins may enhance the development of fibrinous pneumonia after challenge exposure. (Sanford, S. E., "Some Respiratory and Enteric Diseases of Cattle; An Update" *Mod Vet Prac,* 65(4): 265–268 (1984)). Immunization with live vaccines has been generally unsuccessful because of the low antigenicity of *P. haemolytica* and rapid inactivation by the healthy animal. (Henry, C. W., "Shipping fever pneumonia: a new look at an old enemy" *Veterinary Medicine,* 1200–1206 September (1984)).

More recently, attempts to develop a *Pasteurella haemolytica* vaccine have focused on the *P. haemolytica* leukotoxin. In a study to determine the interaction of *P. haemolytica* with bovine neutrophils, results demonstrated that optimal cytotoxin production occurred during the logarithmic phase of bacterial growth for *P. haemolytica* that was grown in a standard tissue culture medium (Baluyut, C. S., et al. "Interaction of *Pasteurella haemolytica* with Bovine Neutrophils: Identification and Partial Characterization of a Cytotoxin", *Am J Vet Res,* Vol. 42, No. 11, pages 1920–1926 (1982)). The authors concluded that ". . . [s]ince this toxin affected the phagocytic cells, it was considered to be a virulence factor." Id. at page 1925.

U.S. Pat. No. 4,957,739 teaches a vaccine containing a purified *P. haemolytica* antigen, such as a leukotoxin component, where the antigen is purified from a cell-free supernatant or obtained by recombinant DNA technology. WO 91/15237 discloses a vaccine composition containing at least one immunogenic polypeptide from the group of *P. haemolytica* fimbrial protein, plasmin receptor protein, a 50K outer membrane protein and leukotoxin. U.S. Pat. No. 5,055,400 discloses DNA encoding *P. haemolytica* A-1 leukotoxin which is used to produce recombinant protein for the preparation of vaccines. U.S. Pat. No. 5,055,400 refers to the protective capability of cytotoxic supernate from *P. haemolytica* and cites U.S. Ser. No. 821,197 filed 27 Jan. 1986 now U.S. Pat. No. 5,165,924 as an example of such a vaccine.

Vaccination of calves with bacteria-free cytotoxic culture supernatant from *P. haemolytica* Type A-1 induced resistance to experimental challenge. (Shewen, P. E., et al. "Immunity to *Pasteurella haemolytica* Serotype 1." In *Proceedings of the North American Symposium on Bovine Respiratory Disease* (R. W. Loan, ed.). Texas A & M University Press, College Station, Tex. pp 480–481 (1984)). A cell-free vaccine containing leukotoxin and serotype specific surface antigens (PRESPONSE® *Pasteurella haemolytica* toxoid: American Cyanamid Co., Wayne, N.J.) was shown to be efficacious in preventing pneumonia in calves vaccinated twice followed by intratracheal challenge with live *P. haemolytica*. (Bechtol, D. T., et al., "Field Trial of a *Pasteurella haemolytica* Toxoid Administered at Spring Branding and in the Feedlot" *Agri-Practice*, Vol. 12, No. 2, pp.6–14 (March/April 1991)).

There remains a need in the art for improved *Pasteurella haemolytica* vaccines, such as a vaccine that confers active immunity in a single dose thereby eliminating the requirement of costly repeat administration and a vaccine that offers the convenience of being administered subcutaneously or intramuscularly.

SUMMARY OF THE INVENTION

There is provided by the invention a novel bacterin-toxoid vaccine capable of inducing immunity in bovine species in one dose against *Pasteurella haemolytica* Type A-1 infection comprising a therapeutically effective amount of *Pasteurella haemolytica* Type A-1 leukotoxoid, capsular antigen, soluble antigens and inactivated cells.

There is further provided by the invention a novel method of making a bacterin-toxoid vaccine capable of inducing immunity in bovine species in one dose against *Pasteurella haemolytica* Type A-1 infection comprising a therapeutically effective amount of *Pasteurella haemolytica* Type A-1 leukotoxoid, capsular antigen, soluble antigens and inactivated cells comprising the steps of: culturing *Pasteurella haemolytica* Type A-1 for a time sufficient for said *P. haemolytica* to reach the late logarithmic phase of growth; inactivating the *P. haemolytica* culture; harvesting the culture fluids comprising the leukotoxoid, capsular antigen, soluble antigens and inactivated *P. haemolytica* cells. Also provided by the invention is the vaccine produced thereby.

Further provided by the invention is a novel method of vaccinating bovine animals comprising administering to said animals a bacterin-toxoid vaccine of this invention.

Further provided by the invention is a novel biologically pure culture of *Pasteurella haemolytica* having all the identifying characteristics of ATCC No. 55318.

DETAILED DESCRIPTION OF THE INVENTION

As used herein, the term "leukotoxin" refers to a soluble toxin produced by actively growing *Pasteurella haemolytica* as taught in the literature. See e.g. U.S. Pat. No. 5,055,400; Canadian patent application 91000097 and Gentry et al., "Neutralizing monoclonal antibodies to *P. haemolytica* leukotoxin affinity-purify the toxin from crude culture supernatants" *Microbial Pathogenesis*, 10: 411–417 (1991), the disclosures of which are incorporated by reference as if fully set forth herein. "Leukotoxoid" is the term used to describe inactivated leukotoxin.

Leukotoxin is alternately referred to in the literature by other identifiers as exotoxin or cytotoxin.

What is meant by "capsular antigen" as used herein refers to a soluble capsular polysaccharide from *P. haemolytica* as described in the literature. See e.g. Inzana, T. J., "Capsules and Virulence in the HAP Group of Bacteria" *Can J of Vet Research*, 54:S22–S27 (1990); and Adlam et al., "Purification, characterization and immunological properties of the serotype-specific capsular polysaccharide of *Pasteurella haemolytica* (serotype Al) organisms" *J Gen Microbiol* 130:2415–2426 (1984), the disclosures of which are incorporated by reference as if fully set forth herein.

What is meant by "soluble antigen" as used herein refers to soluble antigens shed during growth of *P. haemolytica* other than leukotoxin and capsular antigen such as glycoprotease and neuramindase. See e.g. Reggie et al. "Molecular Studies of Ssal, a Serotype-Specific Antigen of *Pasteurella haemolytica* A1", Infection and Immunity, Vol. 59 No.10 3398–3406 (1991).

In one aspect, this invention provides a *Pasteurella haemolytica* Type A-1 bacterin-toxoid vaccine capable of inducing immunity in bovine species in one dose comprising a therapeutically effective amount of leukotoxoid, capsular antigen, soluble antigens and inactivated *Pasteurella haemolytica* Type A-1. The *Pasteurella haemolytica* Type A-1 suitable for use in this invention is believed to be any Type A-1 that is not attenuated. The preferred strain is presently ATCC No. 55318.

The vaccine of this invention can be generally prepared by growing *Pasteurella haemolytica* Type A-1 for optimal leukotoxin production, preferably in a protein fortified cell culture medium, and harvesting the culture fluids during the logarithmic phase.

One of the preferred techniques for preparing the vaccine of the invention is a novel method of making a bacterin-toxoid vaccine capable of inducing immunity in bovine species in one dose against *Pasteurella haemolytica* Type A-1 infection comprising a therapeutically effective amount of *Pasteurella haemolytica* derived leukotoxoid, capsular antigen, soluble antigens and inactivated cells. The method comprises culturing *Pasteurella haemolytica* Type A-1 for a time sufficient for said *Pasteurella haemolytica* to reach the late logarithmic phase of growth.

Standard culture medium suitable for use in the invention is a cell culture medium that is fortified with protein and may be selected by one skilled in the art. One example is RPMI-1640 generally fortified with 3% heat inactivated bovine calf serum, 1% tryptose and 0.1% Tween 80 (polysorbate from Sigma, St. Louis, Mo.) or the like. Growth can be stimulated by the addition of carbohydrates such as glucose to the medium.

The bacteria are grown in the medium from inoculation to the log phase of growth. For optimum leukotoxin production, the late log phase of growth is preferred. This is generally in the range of 2.5 to 6 hours following inoculation of the medium with the bacteria and can be accurately determined by the relationship of optical density to time as is known in the art.

While growth is in the late log phase, an inactivating agent is added to the culture fluids. Preferably, the inactivating agent is a fixative, such as formalin (formaldehyde solution USP), which is usually used at a relatively low concentration of about 0.1 to about 0.5% v/v.

The culture fluids comprising the leukotoxoid, capsular antigen, soluble antigens and inactivated *Pasteurella haemolytica* cells are then harvested by standard techniques known to those in the art such as centrifugation. It is important that the supernatant not be cell-free, thus, methods of harvesting such as filtration which would remove all cells are not within the scope of this invention. The majority of bacteria are removed by centrifugation of the cells to a dense, concentrated aqueous suspension. Centrifugation preferably occurs at a force of about 10,000×g. The methods and conditions to remove the majority of the cells from the culture are within the skill of the art.

The order of inactivation and harvesting in the method of this invention is not believed critical. Presently, it is preferred to inactivate prior to harvesting.

The supernatant is collected and contains from about $10^3$ to about $10^8$ cells/ml of supernatant measured prior to inactivation. The number of cells is difficult to measure and can vary substantially from batch to batch. The lower limit is governed by the necessity of having some cells in the vaccine to assist in providing the immunity conferred by the vaccine of the invention. The upper limit is governed to avoid possible hypersensitization of animals to vaccination. Levels of up to $10^6$ cells/ml have been demonstrated prior to inactivation in the supernatant.

The supernatant produced by this method and used for the vaccine of the invention is a leukotoxoid rich preparation also comprising capsular antigen, soluble antigens and inactivated *Pasteurella haemolytica* Type A-1 cells and cellular debris.

The vaccine of the invention as stated is the culture supernatant which may or may not be concentrated or diluted.

Still other preferred vaccine compositions of this invention result from combining the vaccine of this invention with other vaccinal agents, particularly antigens of other BRDC pathogens. An illustrative example is a vaccine composition formed by the combination of antigens from *Pasteurella multocida, Haemophilus somnus,* Clostridial species, Mycoplasma species, Bovine Respiratory Syncytial Virus, Bovine Viral Diarrhea Virus, Bovine Parainfluenza Type 3 virus.

Vaccines of the invention may be prepared as pharmaceutical compositions containing a therapeutically effective amount of the supernatant as the active ingredient in a nontoxic and sterile pharmaceutically acceptable carrier. A preferred embodiment of the vaccine of the invention is where the vaccine is in freeze-dried form and reconstituted with at least one adjuvant just prior to use. Such a vaccine is preferred as it provides increased stability and reduced free endotoxin, which reduces post-vaccinal systemic reactions. Such adjuvants include, among others, a mineral oil and lecithin emulsion ["AMPHIGEN" mineral oil/lecithin emulsion, Hydronics, Inc.] as taught in U.S. Pat. No. 5,084,269 or other dispersed oils, aluminum hydroxide, muramyl dipeptide, and saponins, such as Quil A. The disclosure of U.S. Pat. No. 5,084,269 is incorporated by reference as if fully set forth herein.

According to the present invention, preferably a pharmaceutical preparation provides a unit dose of between 0.5 and 3 mL, and more preferably approximately 2 mL of a sterile preparation of an immunogenic amount of the active ingredients and carrier.

For purposes of this invention, a therapeutically effective amount of vaccine is that amount which induces immunity in bovine species against *P. haemolytica* Type A-1 infection in one dose. More specifically, this amount can be readily determined by testing a variety of vaccine preparations made in accordance with this invention in cattle and selecting the vaccine preparation that induced immunity in one dose in a statistically significant number of cattle when challenged with *P. haemolytica*. A vaccine induced immunity can be measured by resistance to experimental challenge reflected by decreased or absence of mortality, absence of, or minimal clinical signs, reduction or complete elimination of characteristic lung lesions as is known to those in the art.

A desirable dose regimen involves the administration of one dose of the desired vaccine composition of this invention to confer active immunity. A booster dose is believed desirable whenever subsequent stress or exposure is likely. The mode of administration of the vaccines of the invention may be any suitable route which delivers the vaccine to the host. Presently, the vaccine is preferably administered subcutaneously or by intramuscular injection.

The preferred freeze-dried vaccine is aseptically rehydrated with the adjuvant containing sterile diluent. The vaccine is administered to healthy cattle a minimum of 7–10 days prior to weaning, shipping, or exposure to stress or infectious conditions.

The examples which follow illustrate preferred methods for preparing the vaccine of the invention and for preparing and testing a variety of vaccines. These examples are illustrative only and do not limit the scope of the present invention.

A vaccine embodied by this invention has been commercially available in the United States since about 18 May 1992 and is known as "ONE-SHOT" bacterin-toxoid vaccine (trademark of Pfizer Inc.)

Deposit of Strains Useful in Practicing the Invention

A deposit of biologically pure cultures of the following strain was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or in the case of plasmid-containing strains, lose its plasmid, it will be replaced with a viable culture(s) of the same taxonomic description.

| Strain | Deposit Date | ATCC No. |
|---|---|---|
| *Pasteurella haemolytica* Type A-1 | 9 April 1992 | 55318 |

EXAMPLE 1

Vaccine Preparation

*P. haemolytica* Type A-1 (deposited 9 Apr. 1992 ATCC Accession No. 55318) was grown overnight at 37° C. on brain heart infusion (BHI) agar. Subsequent passages were made in BHI broth in a series of Erlenmeyer flasks, 9 and 19 liter carboys or seed fermentors. The final production medium consists of RPMI 1640 tissue culture medium containing sodium bicarbonate (0.2% w/v), fortified with 3% heat inactivated bovine calf serum, 1% tryptose, and 0.1% Tween 80. Antifoam was included at 0.06% final concentration. The final fermentor was seeded with a 5% inoculum. Cultures were grown for 4.5 hours at 37° C. and the dissolved oxygen content of the culture was monitored and controlled by aeration to a level at 40%. The culture was stirred continuously and was maintained at pH 7.4. Growth was stimulated by the addition of sterile 50% glucose at 2.5, 3.25, and 4.0 hours post-inoculation. At 4.5 hours post-inoculation (at the late logarithmic growth phase), the culture was chilled to 10° C. and inactivated with formalin, added to a final concentration of 0.1% (v/v). Culture fluids were stirred in the fermentor for one hour, and then stored at 4° C. with constant stirring for five days to complete inactivation. Inactivated fluids were centrifuged and the supernatant retained. Sterile 10% Merthiolate and 10% Ethylenediaminetetraacetic Acid (EDTA) were added as preservatives to final concentrations of 0.01% and 0.07%, respectively. The supernatant was stored at −50° C. until it was thawed for assembly.

The supernatant was thawed, and based on results of quantitation assays, was assembled with the addition of sterile phosphate buffered saline. The assembled product was aliquoted into bottles and lyophilized and stored at 4° C.

The duo-phased adjuvant system consists of 5% v/v mineral oil/lecithin emulsion adjuvant sold under the tradename "AMPHIGEN" mineral oil/lecithin emulsion and 12% v/v Aluminum Hydroxide gel, and saline (hereinafter "Adjuvant Diluent). The dual adjuvant diluent was bottled and was used to rehydrate the freeze-dried vaccine.

The vaccine was tested in cattle for protective capabilities by vaccination-challenge experiments.

A relative unit (RU) dose of 1496 per dose of leukotoxoid and 2580 of capsular antigen was assigned to the lyophilized bulk supernatant that was used to prepare the vaccine found to induce immunity in one dose to infection by *P. haemolytica* Type A-1 infection in bovine species as taught herein.

EXAMPLE 2

*Pasteurella haemolytica* Bacterin-Toxoid

Single Vaccination

Dose Titration Study

TABLE 1

One Dose Experimental Design

| Vaccine No. | Number of Animals | Vaccination | Challenge | Necropsy |
|---|---|---|---|---|
| 1 | 5 | Day 0 | Day 14 | Day 20 |
| 2 | 5 | Day 0 | Day 14 | Day 20 |
| 3 | 5 | Day 0 | Day 14 | Day 20 |

TABLE 1-continued

One Dose Experimental Design

| Vaccine No. | Number of Animals | Vaccination | Challenge | Necropsy |
|---|---|---|---|---|
| 4 | 5 | Day 0 | Day 14 | Day 20 |

Animals: 400–550 lbs., beef cattle
Challenge: *P. haemolytica* A-1, heterologous strain, 2.2 × $10^9$ cfu in 500 ml Cherry's Phosphate Buffered Saline (CPBS). Intratracheal administration.
Vaccines: 1. Diluted to 800 RU leukotoxoid and 1380 RU capsular antigen per dose with Adjuvant Diluent. 2 ml dose-intramuscular administration. 2. Diluted to 400 RU leukotoxoid and 690 RU capsular antigen per dose with Adjuvant Diluent. 2 ml dose-intramuscular administration. 3. Diluted to 200 RU leukotoxoid and 345 RU capsular antigen per dose with Adjuvant Diluent. 2 ml dose-intramuscular administration. 4. Placebo (medium control). Diluted as vaccine #3 with Adjuvant Diluent. 2 ml dose-intramuscular administration. 4. Placebo (medium control). Diluted as vaccine #3 with Adjuvant Diluent. 2 ml dose-intramuscular administration.

TABLE II

Summary of Results

| Vaccine No. | No. of Animals | Mean Percent Lung Consolidation | Percent Reduction in Lung Consolidation |
|---|---|---|---|
| 1 | 5 | 0.00 | 100.00 |
| 2 | 5 | 0.18 | 99.30 |
| 3 | 5 | 0.14 | 99.50 |
| 4 | 5 | 27.42 | — |

EXAMPLE 3

*Pasteurella haemolytica* Bacterin-Toxoid

Immunogenicity Study

TABLE III

One Dose Experimental Design

| Vaccine No. | No. of Animals | Vaccination | Challenge | Necropsy |
|---|---|---|---|---|
| 1 (IM) | 20 | Day 0 | Day 14 | Day 20 |
| 1 (SC) | 20 | Day 0 | Day 14 | Day 20 |
| 2 | 10 | Day 0 | Day 14 | Day 20 |

Animals: 400–500 lbs, beef catle
Challenge: *P. haemolytica* A-1, heterologous strain, 1.6 × $10^9$ cfu in 500 ml CPBS. Intratracheal administration.
Vaccines: 1. Diulted to 200 RU leukotoxoid and 345 RU capsular antigen per dose with Adjuvant Diluent. 2 ml dose-intramuscular (IM) or subcutaneous (SC) administration. 2. Placebo (medium control). Diluted as Vaccine #1 with Adjuvant Diluent. 2 ml dose-intramuscular administration.

TABLE IV

Summary of Results

| Vaccine No. | No. of Animals | Mean Percent Lung Consolidation | Percent Reduction in Lung Consolidation |
|---|---|---|---|
| 1 (IM) | 20 | 1.46 | 94.20 |
| 1 (SC) | 20 | 4.77 | 81.20 |
| 2 | 10 | 25.32 | — |

EXAMPLE 4

*Pasteurella haemolytica* Bacterin-Toxoid

TABLE V

One Dose Experimental Design

| Vaccine No. | No. of Animals | Vaccination | Challenge | Necropsy |
|---|---|---|---|---|
| 1 (IM) | 10 | Day 0 | Day 14 | Day 18 |
| 1 (SC) | 10 | Day 0 | Day 14 | Day 18 |
| 2 | 10 | Day 0 | Day 14 | Day 18 |

Animals: 400–550 lbs, beef cattle
Challenge: *P. haemolytica* A-1, 5 ml of 2.5 × $10^9$ cfu/ml. Bilateral transthoracic intrapulmonic injection.
Vaccines: 1. Rehydrated with adjuvant diluent. 2 ml dose-intramuscular (IM) or subcutaneous (SC) administration. 2. Placebo (medium control). Rehydrated with Adjuvant Diluent. 2 ml dose-subcutaneous administration.

TABLE VI

Summary of Results

| Vaccine No. | No. of Animals | Percent Mortality | * Mean Lung Lesion Score |
|---|---|---|---|
| 1 (IM) | 10 | 10.0 | $8.6^A$ |
| 1 (SC) | 10 | 10.0 | $8.5^A$ |
| 2 | 10 | 80.0 | $18.1^B$ |

* Difference between A and B is statistically significant (p < 0.001)

EXAMPLE 5

*Pasteurella haemolytica* Bacterin-Toxoid

Four Month Duration of Immunity Study

Twenty beef calves weighing approximately 450 lbs. (204.5 kg) were selected for this Example. Ten beef calves (Group 1) were vaccinated subcutaneously with one 2 ml. dose of *Pasteurella haemolytica* Bacterin-Toxoid as described below. An additional ten calves (Group 2) were vaccinated subcutaneously with one 2 ml. dose of placebo containing all components of the *Pasteurella haemolytica* Bacterin-Toxoid except for *P. haemolytica* antigens and served as controls. Calves were challenged intratracheally at four months, seven days post-vaccination with a heterologous strain of *P. haemolytica*. (Table VII) Challenge inoculum consisted of a broth culture of *P. haemolytica* containing $1.2 \times 10^7$ colony forming units (cfu) in 500 ml. of Cherry's Phosphate Buffered Saline (CPBS). No animals succumbed to challenge. Animals were necropsied six days post-challenge.

Control animals exhibited a marked increase (statistically significant) in body temperature due to challenge for two days post-challenge while vaccinated animals showed an increase for one day post-challenge. Statistical analysis indicated a significant difference in mean body temperatures at two days post-challenge between vaccinates and controls.

Serum from blood samples collected from each animal by venipuncture was tested for antibody titers to *P. haemolytica* whole cells by an agglutination assay, to leukotoxin by a leukotoxin neutralization assay, and to capsular antigen by an Enzyme-Linked Immunosorbent Assay (ELISA). Samples were collected at pre-vaccination, 4 months post-vaccination (pre-challenge) and six days post-challenge (at time of necropsy). Geometric mean (GM) antibody titers were calculated for each test and results indicated that only GM antibody titers to capsular antigen were signifcantly higher in the vaccinated animals (Group 1) at 4 months post-vaccination and 6 days post-challenge compared to pre-vaccination titers.

At necropsy, lungs were removed and evaluated for lesions characteristics of pneumonic pasteurellosis. (Table VIII) Lungs were scored by weighing affected areas and expressing the percent lung involvement as a percentage of the total weight of the lungs. In addition, lungs were scored by visual inspection including drawings of affected areas. Vaccinated animals had a mean lung consolidation of 2.65% while control animals had a mean lung consolidation of 19.35% when evaluated on the basis of actual weight of affected lung tissue in relation to the weight of the entire lung. Visual scoring of affected lung tissue gave a mean lung consolidation of 1.68% of vaccinated animals and 13.35% for control animals. These results showed an 86.3% reduction in lung lesions in Group 1 compared to Group 2 on the basis of weight, and an 87.42% reduction when visual inspection was used. Statistical analysis showed the difference in lung consolidation between vaccinates and controls to be significant (p<0.05).

The subcutaneous injection sites were carefully examined at necropsy and none of the animals in either group had any visible tissue reactions. Microbial isolations were attempted from lesion-bearing areas of lung tissue. *P. haemolytica* was isolated from lung lesions of 4 of 10 vaccinates and 8 of 10 controls.

These results have shown that this product is safe and efficacious up to four months following administration of a single dose of vaccine. Vaccination of cattle with this product enhanced their resistance to challenge exposure.

TABLE VII

Four Month Duration of Immunity Study Experimental Design

| Vaccine No. | No. of Animals | Vaccination | Challenge | Necropsy |
|---|---|---|---|---|
| 1 | 10 | Day 0 | Day 130 (4 mos., 7 days) | Day 136 |
| 2 | 10 | Day 0 | Day 130 (4 mos., 7 days) | Day 136 |

Animals: Beef Cattle, >600 lbs.
Challenge: *P.haemolytica* A-1. heterologous strain, 1.2 × $10^7$ cfu in 500 ml CPBS. Intratracheal administration.
Vaccines: 1. Pre-licensing serial #1 (Serial No. 24275010 about 305 Ru leukotoxoid and about 529 RU capsular antigen) rehydrated with accompanying Adjuvant Diluent. 2 ml dose-subcutaneous administration. 2. Placebo (medium control) rehydrated with accompanying Adjuvant Diluent. 2 ml dose-subcutaneous administration.

TABLE VIII

Summary of Results

| Vaccine No. | No. of Animals | * Mean Percent Lung Consolidation | Percent Reduction in Lung Consolidation |
|---|---|---|---|
| 1 | 10 | $2.65^A$ | 86.3 |
| 2 | 10 | $19.35^B$ | — |

* Difference between A and B is statistically significant (p = 0.0169)

EXAMPLE 6

*Pasteurella haemolytica* Bacterin-Toxoid

Onset of Immunity Study

Vaccine prepared as described in Example 1. [Leukotoxoid Potency=254 Relative Units/Dose (15 months natural aging), Capsular Antigen Potency=758 Relative Units/Dose]

Thirty beef calves with an average weight of 553 lbs. (251 kg) were selected for this Example. Ten calves (Group A) were vaccinated subcutaneously with one 2 ml. dose of *Pasteurella haemolytica* Bacterin-Toxoid seven days prior to challenge. Another ten calves (Group B) were vaccinated in the same manner with one 2 ml. dose of vaccine three days prior to challenge. An additional ten calves (Group C) were injected seven days prior to challenge via the subcutaneous route with one 2 ml. dose of placebo containing all components of the *Pasteurella haemolytica* Bacterin-Toxoid except for *P. haemolytica* antigens and served as controls. Calves were challenged intratracheally at seven days post-vaccination (Groups A and C) or three days post-vaccination (Group B) with a heterologous strain of *P. haemolytica*. Challenge inoculum consisted of a broth culture of *P. haemolytica* containing $3.0 \times 10^8$ colony forming units (cfu) in 500 ml. of Cherry's Phosphate Buffered Saline (CPBS). One animal in Group B and one in Group C succumbed to challenge and were necropsied as soon as possible. All other animals were necropsied six days post-challenge.

Pre-challenge body temperatures of two-thirds of the animals were 40° C., so no marked increase in body temperature due to challenge was exhibited at any time post-challenge in any of the groups.

Serum from blood samples collected from each animal by venipuncture was tested for antibody titers to *P. haemolytica* whole cells by an agglutination assay, to leukotoxin by a leukotoxin neutralization assay, and to capsular antigen by an Enzyme-Linked Immunosorbent Assay (ELISA). Samples were collected at pre-vaccination, seven days post-vaccination (Groups A and C) and three days post-vaccination (Group B), which was immediately prior to challenge, and six days post-challenge (at time of necropsy). Geometric mean (GM) antibody titers were calculated for each test and results indicated that a significant response to all three antigens was obtained in Group A animals at seven days post-vaccination and no such response was observed in Group B animals at three days post-vaccination or in Group C animals at seven days after placebo administration.

At necropsy, lungs were removed and evaluated for lesions characteristics of pneumonic pasteurellosis. Lungs were scored by weighing affected areas and expressing the percent lung involvement as a percentage of the total weight of the lungs. In addition, lungs were scored by visual inspection including drawings of affected areas. Animals vaccinated seven days prior to challenge had a mean lung consolidation of 12.7%, those vaccinated three days prior to challenge had a mean lung consolidation of 36.1%, while control animals had a mean lung consolidation of 26.6% when evaluated on the basis of actual weight of affected lung tissue in relation to the weight of the entire lung. Visual scoring of affected lung tissue gave a mean lung consolidation of 8.6% for seven-day vaccinates, 28.7% for three-day vaccinates, and 17.8% for placebo controls. These results showed a 52.3% reduction in lung lesions in Group A compared to Group C on the basis of weight, and a 51.7% reduction when visual inspection was used. Statistical analysis showed the difference in lung consolidation between Group A and Group B to be significant ($p<0.05$), but not between Groups A and C. No reduction in lung lesions was observed when comparing three-day vaccinates with placebo controls.

The subcutaneous injection sites were carefully examined at necropsy. Approximately 50% of the animals in all three groups had some evidence of tissue reactions at the injection site. Microbial isolations were attempted from lesion-bearing areas of lung tissue. *P. haemolytica* was isolated from lung lesions of 5 of 10 seven-day vaccinates, 8 of 10 three-day vaccinates, and 7 of 10 placebo controls.

These results have shown that this product, when administered in a single dose, is able to reduce lung damage when animals are challenged seven days post-vaccination, but not at three days post-vaccination. Vaccination of cattle with this product seven days prior to challenge enhanced their resistance to challenge exposure.

CONCLUSION

All studies confirmed the safety of the vaccine. No untoward reactions were observed. Safety was also proved in the administration of three different serials of the vaccine to over 3,000 animals under field conditions. Testing resulted in localized reactions in 3.5% of those vaccinated, with many of those being transient. Few other reactions were observed.

An antigen extinction study was undertaken to determine a nonprotective dosage level of the vaccine. The study was successful indicating a definite relationship between protection and quantity of antigens in the vaccine.

Analysis of the results presented in the studies revealed that this vaccine is efficacious and safe. Vaccination of cattle with this product (either by intramuscular or subcutaneous routes) enhanced their resistance to challenge exposure. This was reflected by a significant reduction in the extent of lung lesions observed with vaccinates compared to control animals. The experimental challenge models employed in these studies leading to the development and testing of this vaccine were severe enough, that under natural conditions, the probability of an animal being exposed to such a level of challenge is remote. It is, therefore, safe to conclude that this vaccine should perform even better under field conditions. It is further intended to use this vaccine as a component of one or more multivalent vaccines containing viral and bacterial components, such as vaccines for bovine respiratory disease complex.

We claim:

1. A bacterin-toxoid vaccine against *Pasteurella haemolytica* Type A-1 infection, comprising a therapeutically effective amount of *Pasteurella haemolytica* Type A-1 leukotoxoid, capsular antigen, soluble antigens, and inactivated cells in a density ranging from about $10^3$ to about $10^8$ cells per ml, which therapeutically effective amount of bacterin-toxoid vaccine provides protection in a bovine species in one dose.

2. The vaccine of claim 1 wherein the leukotoxoid, capsular antigen, soluble antigens and inactivated *Pasteurella haemolytica* are derived from strain ATCC No. 55318.

3. The vaccine of claim 1 further comprising a therapeutically effective amount of one or more additional antigens of pathogens of bovine respiratory diseases.

4. The vaccine of claim 1 wherein the vaccine is freeze-dried and rehydrated prior to use with at least one adjuvant.

5. The vaccine of claim 4 further comprising two adjuvants.

6. The vaccine of claim 5, wherein the adjuvants comprise aluminum hydroxide gel and a mineral oil/lecithin emulsion.

7. A method of making a bacterin-toxoid vaccine which provides protection in a bovine species in one dose against *Pasteurella haemolytica* Type A-1 infection, comprising the steps of: culturing *Pasteurella haemolytica* Type A-1 for a time sufficient for said *P. haemolytica* culture to reach the late logarithmic phase of growth; inactivating the *P. haemolytica* culture; and harvesting culture supernatant therefrom comprising leukotoxoid, capsular antigen, soluble antigens, and inactivated *P. haemolytica* cells at a density ranging from about $10^3$ to about $10^8$ cells per ml.

8. The method of claim 7 wherein the *P. haemolytica* is strain ATCC No. 55318.

9. The method of claim 7 wherein said time sufficient for said *P. haemolytica* to reach the late logarithmic phase of growth is about 2.5 to 6 hours.

10. The method of claim 7 wherein the *P. haemolytica* culture is inactivated with formalin.

11. The method of claim 7 wherein the supernatant is harvested by centrifugation.

12. The method of claim 7 wherein the *P. haemolytica* is cultured in a protein fortified cell culture medium.

13. The method of claim 12 wherein the cell culture medium comprises RPMI-1640 and about 3% bovine calf serum, about 1% Tryptose and 0.1% Tween 80.

14. A bacterin-toxoid vaccine against *Pasteurella haemolytica* Type A-1 infection produced by culturing *P. haemolytica* Type A-1 for a time sufficient for said *P. haemolytica* culture to reach the late logarithmic phase of growth; inactivating the *P. haemolytica* culture; and harvesting the culture supernatant therefrom comprising leukotoxoid, capsular antigen, soluble antigens, and inactivated *P. haemolytica* cells at a density ranging from about $10^3$ to about $10^8$ cells per ml.

15. The vaccine of claim 14 wherein the vaccine is freeze-dried and is reconstituted prior to use with at least one adjuvant.

16. The vaccine of claim 15, wherein the freeze-dried vaccine is reconstituted with two adjuvants.

17. The vaccine of claim 16, wherein the adjuvants are aluminum hydroxide gel and a mineral oil/lecithin emulsion.

18. A method of vaccinating bovine animals against *Pasteurella haemolytica* consisting of administering to said animals a single dose of a bacterin-toxoid vaccine comprising a therapeutically effective amount of *P. haemolytica* Type A-1 leukotoxoid, capsular antigen, soluble antigens, and inactivated cells.

19. The method of claim 18 wherein said administration is intramuscular or subcutaneous.

20. The method of claim 18 wherein the vaccine is in freeze-dried form and is reconstituted prior to use with at least one adjuvant.

21. The method of claim 20 wherein the vaccine comprises two adjuvants.

22. The method of claim 21, wherein the adjuvants are aluminum hydroxide gel and a mineral oil/lecithin emulsion.

23. A biologically pure culture of *Pasteurella haemolytica* having all the identifying characteristics of ATCC No. 55318.

24. The method of claim 18, wherein the bacterin-toxoid vaccine is prepared by inactivating a culture of *P. haemolytica* in the late logarithmic phase of growth with formalin.

25. A bacterin-toxoid vaccine composition against *Pasteurella haemolytica* Type A-1 infection, consisting essentially of a therapeutically effective amount of *P. haemolytica* Type A-1 leukotoxoid, capsular antigen, soluble antigens, inactivated cells in a density ranging from about $10^3$ to about $10^8$ cells per ml, aluminum hydroxide gel and a mineral oil/lecithin emulsion, said vaccine providing protection in a bovine species in one dose.

26. A method of making a bacterin-toxoid vaccine which protection in a bovine species in one dose against *Pasteurella haemolytica* Type A-1 infection, comprising the steps of: culturing *P. haemolytica* Type A-1 for a time sufficient for said culture to reach the late logarithmic phase of growth; harvesting culture supernatant therefrom comprising leukotoxin, capsular antigen, soluble antigens, and *P. haemolytica* cells at a density ranging from about $10^3$ to about $10^8$ cells per ml; and adding an inactivating agent.

27. The method of claim 26, wherein the inactivating agent is formalin.

28. A bacterin-toxoid vaccine against *Pasteurella haemolytica* Type A-1 infection produced by culturing *P. haemolytica* Type A-1 for a time sufficient for said *P. haemolytica* culture to reach the late-logarithmic phase of growth; harvesting culture supernatant therefrom comprising leukotoxin, capsular antigen, soluble antigens, and *P. haemolytica* cells at a density ranging from about $10^3$ to about $10^8$ cells per ml; and adding an inactivating agent.

29. The bacterin-toxoid vaccine of claim 28, wherein the inactivating agent is formalin.

* * * * *